United States Patent [19]
Rodriguez del Val

[11] Patent Number: 6,042,379
[45] Date of Patent: Mar. 28, 2000

[54] DENTAL RAISING FORCEPS FOR THE REARMOST UPPER MOLARS OR THEIR REMAINS

[75] Inventor: José Maria Rodriguez del Val, Burgos, Spain

[73] Assignee: Corporacion O.I.B., S.L., Spain

[21] Appl. No.: 09/234,647

[22] Filed: Jan. 21, 1999

[30] Foreign Application Priority Data

Jan. 27, 1998 [ES] Spain ..................................... 9800147

[51] Int. Cl.[7] .................................................... A61C 3/14
[52] U.S. Cl. ............................................................ 433/159
[58] Field of Search ..................................... 433/159, 160

[56] References Cited

U.S. PATENT DOCUMENTS

| 1,675,815 | 7/1928 | Miller | 433/159 |
| 2,632,248 | 3/1953 | Kohler | 433/160 |
| 2,674,800 | 4/1954 | Osborn et al. | 433/159 |

*Primary Examiner*—John J. Wilson
*Attorney, Agent, or Firm*—Fulwider Patton Lee & Utecht, LLP

[57] ABSTRACT

Dental raising forceps for the posterior upper molars or their remains, in the upper arcade, which has a passive part (1) and a hinge (2) that are conventional, together with a contra-angled part in bayonet form (3), and which terminates in certain moving jaws (4), in a circumferential arch, concave on the inside and symmetrical, and the cross-section of which gradually diminishes until it terminates in two points, (assuming the shape of a pair of bull's horns) which makes it possible to insert it between the last two dental pieces and which when it is moved gives rise to the distal (backwards) luxation of the last molar and its consequent loosening.

6 Claims, 1 Drawing Sheet

DENTAL RAISING FORCEPS FOR THE REARMOST UPPER MOLARS OR THEIR REMAINS

BACKGROUND OF THE INVENTION

1. Field of the Invention

The present invention relates to dental raising forceps for the posterior upper molars or their remains.

2. Description of Related Art

A multitude of dental forceps are known which entrap and move dental pieces or raise them to the same end, being inserted between two pieces or roots and/or between these and the maxillary bone.

The forceps are pincers, formed of a passive part which can be manully manipulated, a hinge and an active part that entraps the piece.

The raisers take the form of levers or straight or angled punches, pointed or sharp-edged; flat or grooved, of different lengths and with handles of diverse shapes to permit manipulation.

The forceps for upper dental pieces are straight or curved in different ways in their moving and unmoving parts, or, for the rearmost molars, with a contra-angled bayonet shaped active part to facilitate entrapment of the piece without forcing or damaging the lips or the corners of the mouth.

The case which we propose is the extraction of the third upper molar, or wisdom tooth.

On occasions there are difficulties in entrapping such pieces using conventional bayonet forceps, if the crown of the molar is in a very posterior position, not very prominent, displaced towards the vestibule or palate, or if it is more or less destroyed; causing it to fracture when it is entrapped.

On other occasions, even when it is possible to entrap the molar, its large curved roots give it a strength that is hard to overcome, and it is very difficult to move the latter without breaking them.

The use of a raiser to try to loosen the piece or luxate it is also very difficult this far back in the mouth, and runs the risk of causing tears or perforations of the maxillary sinus, or even of pushing some remains of the roots towards the said sinus instead of raising them, or giving rise to too wide a luxation of the piece or root and thereby causing its total extraction and subsequent fall into the oral pharynx and possible swallowing of the same.

SUMMARY OF THE INVENTION

The present invention consists of bayonet forceps, the moving parts of which terminate in two pointed ends (jaws), progressively more half-moon in shape, until they end in two rounded and symmetrical points having the appearance of two bull's horns, and which when they are inserted between the second and third upper molars, whether the latter has emerged completely or incompletely, located in line with the arcade or displaced towards the vestibule or palate and with its crown complete or more or less destroyed, gives rise when activated to distal luxation of the last molar or remains of the root together with the resulting loosening and elevation, thereby facilitating its entrapment by conventional forceps and smooth safe extraction.

Figures 1A, 1B:
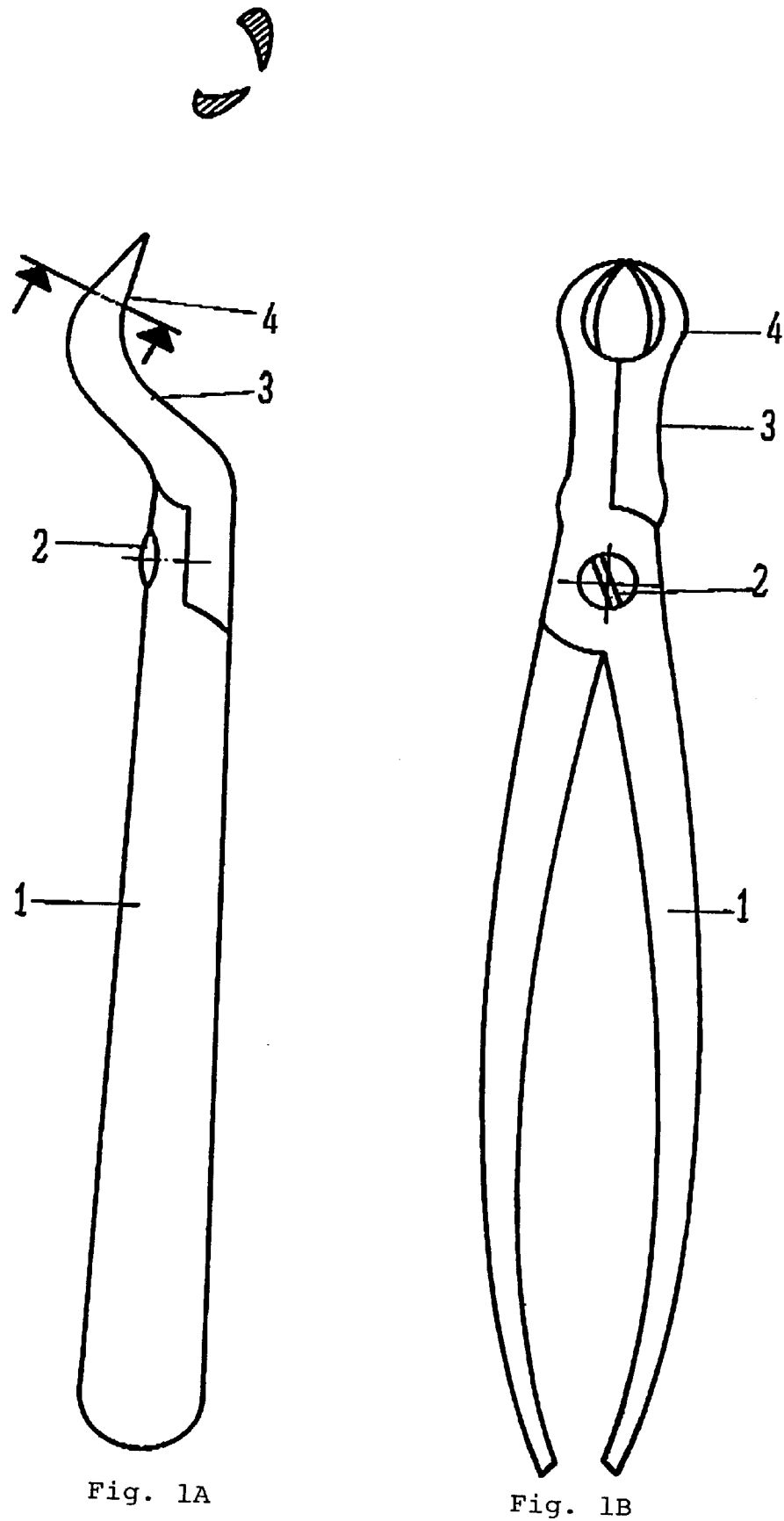
FIG. 1A is a side elevational view of a preferred embodiment of bayonet forceps according to the invention, with a sectional detail view of the tips of the jaws of the bayonet forceps.
FIG. 1B is a top plan view of the bayonet forceps of FIG. 1A.

A preferred embodiment of the raising upper horn bayonet forceps for bringing about the luxation of the third molar or the remains of roots of the last molar or the remains of roots at both distal (posterior) extremes of the upper arcade is illustrated in FIGS. 1A and 1B.

DETAILED DESCRIPTION OF THE PREFERRED EMBODIMENT

This forceps has a passive part (1) and hinge (2) that are conventional, together with a contra-angled active part in bayonet form (3) that ends in two extremes (active jaws) (4) which curve symmetrically in an arch, the circumference and cross-section of which progressively diminish until they end in two points which come together and which give it an appearance like the two horns of a bull, when the forceps is closed.

These points may be inserted between the second and third upper molars, whether or not the latter has emerged completely or if its crown is in line with the arcade or is leaning sideways out of line towards the vestibule or palate, and also if the said crown is whole or is more or less destroyed by caries or fracture; giving rise on being moved to extraction of the roots and luxation distally (rearward) with the resulting loosening and raising of the molar or remains of roots, so that these may be easily entrapped in conventional forceps and smoothly extracted.

This tool will be manufactured of material that is sufficiently strong, be it metal, plastic or ceramic.

The ideal cross-section for this tool to be inserted between the molars is half-moon in form, with a rough inner edge, facilitating this, and a frontal surface that is convex with a concave rear surface, to hold and direct the crown of the molar distally (rearward).

The materials employed in the manufacture of the object corresponding to this invention are independent of the same, as are its length or the degrees of the angles used or the curves of the active jaws, or whether surfaces are smooth or striated.

Whether the curvature or length of the active jaw is equal to or different from those of the other one is also independent of the object of this invention. This is also the case for: the distance between both points when closed, and possible variations in cross-section (circular, elliptical, triangular, flat, spindle-shaped, etc.) which tend to bring about the same effect of luxation; the length and degree of the angle of the first section of the moving part (3); and variations to the passive parts and hinge and all of the accessory details which may be present and which to not affect its essential nature.

What is claimed is:

1. Dental raising forceps for the posterior upper molars or their remains, characterized in that they have a moving part which consists of two arms connected together by a hinge, from which two moving jaws emerge, said jaws extending at opposing angles, said jaws being half-moon shaped in cross-section and with narrow angled edges on the inside and outside, and with two rounded surfaces consisting of a frontal convex surface and a posterior concave surface for guiding the last molar backwards, the cross-section of said jaws gradually diminishing conically to terminate in two points, while simultaneously gradually curving such that each jaw first curves away from and then curves towards the other assuming the shape of a pair of bull's horns when the forceps is in closed position.

2. Forceps according to claim 1, wherein said arms are angled.

3. Forceps according to claim 1, wherein said arms are curved.

4. Forceps according to claim 1, wherein said each jaw curves in a semi-circular arc away from and then toward the other.

5. Forceps according to claim 1, wherein said each jaw curves in an elliptical arc away from and then toward the other.

6. Dental forceps for rearward luxation and elevation of posterior upper molars or their remains, comprising in combination:

first and second forceps members pivotally connected together at a hinge, each of said forceps members including an elongated handle portion extending in a plane of the dental forceps on one side of the hinge, and an opposing portion on the other side of the hinge, the opposing portion comprising an elongated intermediate bayonet portion extending from the hinge, and a jaw portion extending from the intermediate bayonet portion, said intermediate bayonet portions of said first and second forceps members extending from said handle portions of said forceps members at a first angle from the plane of the dental forceps, and said jaw portions of said first and second forceps members extending from the respective bayonet portions at a second angle back toward the plane of the dental forceps, each of said jaw portions having a half-moon shaped cross-section arcing outwardly and together forming a cup shape, and gradually tapering from the respective intermediate bayonet portions to terminate in points that meet when the dental forceps is in a closed position, whereby said jaws can be inserted between two adjacent upper molars for rearward luxation and elevation of the rearmost of the two adjacent upper molars.

* * * * *

UNITED STATES PATENT AND TRADEMARK OFFICE
CERTIFICATE OF CORRECTION

PATENT NO. : 6,042,379
DATED : Mar. 28, 2000
INVENTOR(S) : Jose' Maria Rodriguez del Val It is certified that error appears in the above-identified patent and that said Letters Patent is hereby corrected as shown below:

Column 2, lines 3-7, delete entire paragraph beginning with "A preferred...." and move said paragraph to become a new paragraph after column 2, line 35, "distally (rearward),"

Signed and Sealed this

Sixth Day of February, 2001

Attest:

Attesting Officer

Q. TODD DICKINSON

Director of Patents and Trademarks